US008252279B2

(12) United States Patent
Caviedes et al.

(10) Patent No.: US 8,252,279 B2
(45) Date of Patent: *Aug. 28, 2012

(54) METHODS FOR CELL THERAPY

(75) Inventors: Pablo Caviedes, Santiago (CL); Raul Caviedes, Santiago (CL); Thomas B. Freeman, Tampa, FL (US); Juan A. Asenjo, Santiago (CL); Barbara A. Andrews, Santiago (CL); Dario Sepúlveda, Santiago (CL); Christian Arriagada, Santiago (CL); Julio Salazar Rivera, Santiago (CL)

(73) Assignee: University of South Florida, Tampa, FL (US)

( * ) Notice: Subject to any disclaimer, the term of this patent is extended or adjusted under 35 U.S.C. 154(b) by 1268 days.

This patent is subject to a terminal disclaimer.

(21) Appl. No.: 11/951,529

(22) Filed: Dec. 6, 2007

(65) Prior Publication Data

US 2008/0089865 A1 Apr. 17, 2008

Related U.S. Application Data

(62) Division of application No. 10/815,388, filed on Mar. 31, 2004, now Pat. No. 7,323,333.

(60) Provisional application No. 60/459,506, filed on Mar. 31, 2003.

(51) Int. Cl.
C12N 5/02 (2006.01)
(52) U.S. Cl. .................. 424/93.7; 435/383; 435/368
(58) Field of Classification Search .................. None
See application file for complete search history.

(56) References Cited

U.S. PATENT DOCUMENTS

| 5,219,752 | A | 6/1993 | Takazawa et al. |
| 5,411,883 | A | 5/1995 | Boss et al. |
| 5,981,165 | A | 11/1999 | Weiss et al. |
| 5,994,126 | A | 11/1999 | Steinman et al. |
| 6,399,369 | B1 | 6/2002 | Weiss et al. |
| 2003/0185870 | A1 | 10/2003 | Grinstaff et al. |

FOREIGN PATENT DOCUMENTS

| WO | WO 00/05343 A2 | 2/2000 |
| WO | WO 02/14479 A2 | 2/2002 |

OTHER PUBLICATIONS

Cheung, W.M.W. et al. "Production of Human CNS Neurons from Embryonal Carcinoma Cells Using a Cell Aggregation Method" *BioTechniques*, May 1999, pp. 946-954, vol. 26.
Peaire, A.E. et al. "Production of dopaminergic neurons for cell therapy in treatment of Parkinson's disease" *Journal of Neuroscience Mthods*, 2003, pp. 61-74, vol. 124.
Romero-Ramos, M. et al. "Neuronal Differentiation of Stem Cells Isolated From Adult Muscle" *Journal of Neuroscience Research*, 2002, pp. 894-907, vol. 69.
Tzeng, S. "Neural Progenitors Isolated from Newborn Rat Spinal Cords Differentiate into Neurons and Astroglia" *Journal of Biomedical Science*, 2002, pp. 10-16, vol. 9.
Exam Report dated Jul. 28, 2009 in European Application No. 04749667.4, pp. cover, 1-10.
Allen, D.D. et al. "Impaired cholinergic function in cell lines derived from the cerebral cortex of normal and trisomy 16 mice" *Eur. J. Neurosci.*, 2000, 12:3259-3264.
Allen, D.D. et al. "A dorsal root ganglia cell line derived from trisomy 16 fetal mice, a model for Down syndrome" *NeuroReport*, 2002, 13:491-496.
Andrews, B.A. et al. "Factors for the Optimization of the Culture of Neuronal Cell Lines for the Development of Cell Transplant Material" poster presented at the Cell Culture & Engineering Conference in Snowmass, CO, Apr. 1-6, 2002.
Arriagada, C. et al. "Studies of aminochrome toxicity in a mouse derived neuronal cell line: is this toxicity mediated via glutamate transmission?" *Amino Acids*, 2000, 18:363-373.
Barros, V.G. et al. "Corticosterone down-regulates dopamine $D_4$ receptor in a mouse cerebral cortex neuronal cell line" *Neurotoxicity Res.*, 2003, 5(5):369-374.
Bhadriraju, K. and Hansen, L.K. "Hepatocyte adhesion, growth and differentiated function on RGD-containing proteins" *Biomaterials*, 2000, 21:267-272.
Cárdenas, A. et al. "Cell lines derived from hippocampal neurons of the normal and trisomy 16 mouse fetus (a model for down syndrome) exhibit neuronal markers, cholinergic function, and functional neurotransmitter receptors" *Experimental Neurology*, 2002, 177:159-170.
Cárdenas, A. et al. "Establishment and characterization of immortalized neuronal cell lines derived from the spinal cord of normal and trisomy 16 fetal mice, an animal model of Down syndrome" *J. Neurosci. Res.*, 2002, 68:46-58.
Cárdenas, A.M. et al. "Calcium signals in cell lines derived from the cerebral cortex of normal and trisomy 16 mice" *NeuroReport*, 1999, 10:363-369.
Carmona, M.T. and Caviedes, R. "Effects of factors derived from a tumor clonal cell line on DNA synthesis of transformed and non transformed cells" *Cell Biol Int Rep.*, 1985, 9(3):209-218.
Caviedes, P. et al. "Calcium fluxes, ion currents and dihydropyridine receptors in a new immortal cell line from rat heart muscle" *J. Mol. Cell Cardiol.*, 1993, 25:829-845.
Caviedes, R. and Stanbury, J.B. "Studies on a cell line from a functional rat thyroid tumor in continuous culture" *Endocrinology*, 1976, 99:549-554.
Caviedes, R. et al. "Tetrodotoxin-sensitive sodium channels in a continuously cultured cell line derived from the adult rat cerebellum" *Brain Res.*, 1986, 365(2):259-268.

(Continued)

Primary Examiner — Allison Ford
(74) Attorney, Agent, or Firm — Saliwanchik, Lloyd & Eisenschenk

(57) ABSTRACT

The subject invention pertains to materials and methods for inhibiting process formation and extension by cells in culture. The subject invention further includes cultures of process-forming cells wherein formation and extension of processes have been inhibited. In another aspect, the subject invention concerns methods of transplantation using process-forming cells that have been cultured by the process-inhibiting methods of the invention.

24 Claims, 2 Drawing Sheets

OTHER PUBLICATIONS

Caviedes, R. et al. "Identification of kallikrein in cultures of adult renal cells" *Cell Biol Int Rep*, 1987, 11(10):735-743.

Caviedes, R. et al. "Ion channels in a skeletal muscle cell line from a Duchenne muscular dystrophy patient" *Muscle Nerve*, 1994, 17(9):1021-1028.

Chen, G. et al. "Photoimmobilization of sulfated hyaluronic acid for antithrombogenicity" *Bioconj. Chem.*, 1997, 8:730-734.

Chiu, D.T. et al. "Patterned deposition of cells and proteins onto surfaces by using three-dimensional microfluidic systems" *Proc. Acad. Sci. USA*, 2000, 97:2408-2413.

Clémence, J.F. et al. "Photoimmobilization of a bioactive laminin fragment and pattern-guided selective neuronal cell attachment" *Bioconjug. Chem.*, 1995, 6:411-417.

Delamarche, E. et al. "Patterned diversity of immunoglobulins to surfaces using microfluidic networks" *Science*, 1997, 276:779-781.

Eagle, H. et al. "Myo-inositol as an essential growth factor for normal and malignant human cells in tissue culture" *J. Biol. Chem.*, 1956, 123:845-847.

Eagle, H. "Media for Animal Cell Culture" Tissue Culture Association Manual, 1976, 3:517-519.

Eagle, H. "Amino acid metabolism in mammalian cell cultures" *Science*, 1959, 130:432-437.

Eagle, H. "Nutrition needs of mammalian cells in tissue culture" *Science*, 1955, 122:501-504.

Folch, A. and Toner, M. "Cellular micropatterns on biocompatible materials" *Biotechnol. Prog.*, 1998, 14:338-392.

Horacek, M.J. et al. "Adult adenohypophysial cells express $\beta_1$ integrins and prefer laminin during cell-substratum adhesion" *In Vitro Cell. Dev. Biol.*, 1994, 30A:35-40.

Lernhardt, W. and Spear, D. "Improved adherent mammalian cell transfection with ProNectin™ F recombinant attachment factor" *Strategies in Molecular Biology*, 1993, 5:48-50.

Liberona, J.L. et al. "Expression of ion channels during differentiation of a human skeletal muscle cell line" *J. Muscle Res. Cell Motility*, 1997, 18:587-598.

Liberona, J.L. et al. "Differences in both inositol 1,4,5-trisphosphate mass and inositol 1,4,5-trisphosphate receptors between normal and dystrophic skeletal muscle cell lines" *Muscle & Nerve*, 1998, 21:902-909.

Liu, V.A. et al. "Engineering protein and cell adhesivity using PEO-terminated triblock polymers" *J. Biomed. Mater. Res.*, 2002, 60:126-134.

Lom, B. et al. "A versatile technique for patterning biomolecules onto glass coverslips" *J. Neurosci. Methods*, 1993, 50:385-397.

Lwebuga-Mukasa, J.S. "A $Mn^{2+}$-enhanced, RGD-dependent adhesion technique for isolation of adult rat type II alveolar epithelial cells for immediate functional studies" *Am. J. Respir. Cell Mol. Biol.*, 1994, 10:347-354.

Maung, K. et al. "Requirement for focal adhesion kinase in tumor cell adhesion" *Oncogene*, 1999, 18:6824-6828.

Needels, D.L. et al. "Long-term support by injured brain extract of a subpopulation of ciliary ganglion neurons purified by differential adhesion" *Neurochem. Res.*, 1987, 12(10):901-907.

Paris, I. et al. "Copper neurotoxicity is dependent on dopamine-mediated copper uptake and one-electron reduction of aminochrome in a rat substantia nigra neuronal cell line" *J. Neurochem.*, 2001, 77:519-529.

Ruoslahti E. and Pierschbacher, M.D. "New perspectives in cell adhesion: RGD and integrins" *Science*, 1987, 238:491-497.

Salazar, J. et al. "Intrastriatal implantation of RCSN adult rat substantia nigra-derived cells reverts rotational behaviour in 6OH dopamine lesioned rats" Abstract No. 300.8, Society for Neuroscience, Washington, D.C., 2003.

Singhvi, R. et al. "Engineering cell shape and function" *Science*, 1994, 264:696-698.

Stedronsky, E.R. et al. "Injection molding of ProNectin® dispersed in polystyrene for the fabrication of plastic ware activated towards attachment of mammalian cells" *Materials Research Society Symposium Proceedings*, 1994, 330:157-164.

Varani, J. et al. "Use of recombinant and synthetic peptides as attachment factors for cells on microcarriers" *Cytotechnology*, 1993, 13:89-98.

Zheng, J. et al. "Measurements of growth cone adhesion to culture surfaces by micromanipulation" *J. Cell Biol.*, 1994, 127(6, Part 2):2049-2060.

Eagle, H. et al. "myo-inositol as an essential growth factor for normal and malignant human cells in tissue culture" *J. Biol. Chem.*, 1957, 226:191-205.

Hartung, T. et al. "Good cell culture practice. ECVAM good cell culture practice task force report 1" *ATLA*, 2002, 30:407-414.

Studer, L. et al. "Transplantation of expanded mesencephalic precursors leads to recovery in parkinsonian rats" *Neurosci.*, 1998, 1:290-295.

Sigma-Aldrich product information for product No. M0518: Minimum Essential Medium Eagle; Nov. 1998.

Sigma-Aldrich product information for product No. M0518: Minimum Essential Medium Eagle; Apr. 2006.

Bjerkvig, R. et al. "Reaggregation of fetal rat brain cells in a stationary culture system I: Methodology and cell identification" *In Vitro Cellular & Dev. Biol.*, 1986, 22(4):180-192.

Marchal, S. et al. "Neurosphere formation of NTera-2 cells grown in serum-free medium: Comparison with neurospheres derived from mouse neural stem cells" Program No. 726.12, Society for Neuroscience, Nov. 2, 2002, Washington, D.C.

Suarez-Isla, B. et al. "Blockers of calcium permeability inhibit neurite extension and formation of neuromuscular synapses in cell culture" *Dev. Brain Res.*, 1984, 14:263-270.

Turner, D. et al. "Magnesium-dependent attachment and neurite outgrowth by PC12 cells on collagen and laminin substrata" *Dev. Biol.*, 1987, 121:510-525.

METHODS FOR CELL THERAPY

CROSS REFERENCE TO RELATED APPLICATION

The present application is a divisional of U.S. application Ser. No. 10/815,388, filed Mar. 31, 2004, now U.S. Pat. No. 7,323,333, which claims the benefit of U.S. Provisional Application Ser. No. 60/459,506, filed Mar. 31, 2003, each of which is hereby incorporated by reference herein in its entirety, including any figures, tables, nucleic acid sequences, amino acid sequences, or drawings.

BACKGROUND OF THE INVENTION

The establishment of functional neuronal cell lines that permanently grow in culture remains a challenge for tissue culture laboratories. Conventional neuronal culture preparations form processes, called neurites, which are severed at the time of harvest for neural transplant. Unfortunately, detachment of neurites from the culture vessels causes axotomy, which greatly reduces viability of the cells in vitro and in vivo, jeopardizing the success of cell therapy using these cells. Also, unfortunately, in vitro manipulation of cells prior to transplant is usually desirable in order to achieve the differentiated phenotype of the cells. In the case of neurons, this usually requires neurite growth.

Accordingly, it would be advantageous to identify a cell culture protocol that allows cell differentiation in the absence of process formation, thereby optimizing cell viability and function.

BRIEF SUMMARY OF THE INVENTION

The subject invention pertains to materials and methods for inhibiting process formation and extension by cells in culture. The method of the subject invention involves culturing one or more process-forming cells under conditions that are inhibitory to the formation and extension of processes. In one embodiment, the method of the subject invention involves culturing one or more process-forming cells, wherein the culture contains no cell attachment factors that promote adhesion of the cells to a solid substrate. In another embodiment, the method of the subject invention involves culturing one or more process-forming cells on a solid substrate, such as a culture vessel, that has not been treated to promote cell attachment and lacks cell attachment factors on its surface that promote adhesion of the cells thereto. The culture vessel can be, for example, a Petri dish, flask, bottle, plate, tube, vial, etc., which can be welled or unwelled. Preferably, the solid substrate is a plastic vessel lacking any charged molecules. More preferably, the culture vessel is a microbiological plate.

In another embodiment, the method of the subject invention involves culturing one or more process-forming cells under low calcium or calcium-free conditions. For example, the process-forming cells can be cultured in low calcium ($Ca^{2+}$) or calcium-free media. In another embodiment, the method of the subject invention involves culturing one or more process-forming cells, wherein the culture contains no cell attachment factors that promote adhesion of the cells to a solid substrate, and the culture media is low calcium or calcium-free. In another embodiment, the method of the subject invention involves culturing one or more process-forming cells on a solid substrate lacking attachment factors, as described above, and wherein the cells are cultured under low calcium or calcium-free conditions.

In another aspect, the subject invention pertains to cell therapy using cells cultured according to the methods of the subject invention. A method for transplanting process-forming cells is carried out by culturing the cells according to the methods of the subject invention and subsequently administering the cells to a host, such as a human or animal.

Examples of process-forming cells that can be cultured using the methods of the subject invention include, but are not limited to, neurons, glial cells, muscle cells (such as cardiac muscle cells and skeletal muscle cells), cells of connective tissue (such as fibroblasts), and endothelial cells. The process-forming cells to be cultured can be at various stages of differentiation.

The subject invention also pertains to cell cultures comprising process-forming cells in the absence of cell attachment factors. Preferably, the process-forming cells are supported by a solid substrate lacking attachment factors, such as a microbiological plate, wherein the formation or extension of processes by the cells is inhibited. In another embodiment, the cell culture of the subject invention comprises a culture vessel or other solid support that contains or supports process-forming cells, wherein the cell culture is free of calcium or contains a low concentration of calcium, wherein the formation or extension of processes by the cells is inhibited by the low calcium concentration. Preferably, the cell culture comprises culture media that is either calcium-free or a low calcium media. In another embodiment, the cell culture comprises process-forming cells, a solid substrate lacking attachment factors, as described above, wherein the cell culture is free of calcium or contains a low concentration of calcium. For example, the cell culture can comprise process-forming cells, a solid substrate lacking attachment factors, and calcium-free or low calcium culture media.

DETAILED DESCRIPTION OF THE INVENTION

Figure 1:
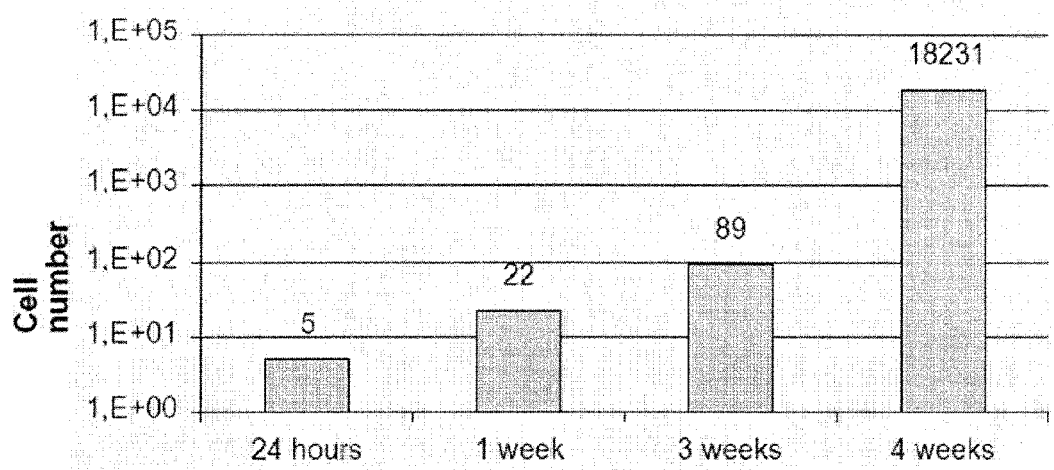
FIG. 1 shows the evolution in the size of RCSN-3 cell aggregates cultured using the method of the subject invention.

The method of the subject invention involves culturing one or more process-forming cells under conditions that are inhibitory to the formation and extension of processes. According to the method of the subject invention, process-forming cells are cultured in the absence of cell attachment factors.

In one embodiment, the method of the subject invention involves culturing one or more cells on a solid substrate, such as a culture vessel, that has not been treated to promote cell attachment and lacks any cell attachment factors on its surface that promote adhesion of the cells thereto. Preferably, there are no cell attachment factors within the cell culture, e.g., no attachment factors associated on or within the substrate, or within the culture medium. The culture vessel can be, for example, a Petri dish, flask, bottle, plate, tube, vial, etc., which can be welled or unwelled. The substrate can be composed of any material lacking cell attachment factors. For example, the substrate can be composed of one or more polymers or copolymers lacking cell attachment factors. Preferably, the substrate is composed of plastic, such as polystyrene, polyethylene, polypropylene, or polycarbonate. More preferably, the solid substrate is a plastic vessel lacking any charged molecules that promote cell adhesion. Yet more preferably, the culture vessel is a microbiological plate (also referred to as a bacteriological plate). Other substrates, such as two-dimensional or three-dimensional scaffolds, implants, microcarriers (e.g., beads composed of glass, plastic, or other materials), fiber beds, hollow fibers, stacked plate modules, or cell factories can also be utilized. Preferably, the substrate has a surface topography that is sufficiently smooth (lacking roughness) so as to prevent cell attachment. Therefore, random roughness, grooves, and pillars/spikes are not present or their presence is minimized.

As used herein, the term "cell attachment factor", or grammatical variations thereof, includes any molecule or chemical moiety that promotes passive or active adhesion of a cell to a substrate surface. Culture substrates that lack cell attachment factors are not formulated, coated, or otherwise associated with cell attachment factors. Likewise, as used herein, the term "cell attachment treatment", or grammatical variations thereof, includes any physical and/or chemical treatment or conditioning of a substrate that promotes passive or active adhesion of a cell to a substrate surface. Therefore, the substrates to be used in the methods of the subject invention exclude those that have been physically or chemically treated or conditioned to promote or facilitate cell adhesion to the substrate, or to otherwise include a cell attachment factor. These substrates are known in the art as "cell culture treated", "tissue culture treated", "cell growth surface treated", or "TC plastic". As described in more detail below, since cells (and particularly proteins and other biomolecules on the cell surface) tend to adsorb to surfaces through hydrophobic and ionic interactions, these "treated" culture vessels are usually treated by a process that involves physical and/or chemical modification of the vessel surface, such that charged molecules are associated with the vessel surface, which can make the surface more hydrophilic (less hydrophobic) and conducive to attachment (adhesion) of cells, particularly anchorage-dependent cells.

The most commonly selected plastic for assay plates or culture vessels is polystyrene, because of its pure optical clarity and range of surface properties. As a long chain hydrocarbon, non-modified polystyrene tends to repel water and hydrophilic molecules and attract hydrophobic molecules. Hydrophobic molecules adsorb to the polystyrene surface as a result of intermolecular interaction, mainly van der Waals forces. Large biomolecules that are hydrophilic will typically have stretches of hydrophobic regions that allow the molecule to adsorb to the polystyrene surface. The surface of polystyrene substrates can be physically modified ("cell culture treated" or "tissue culture treated") through a number of methods. By applying energy (electrical discharge, UV irradiation, e-beam, and gamma irradiation), free radicals are formed in the polystyrene molecule, breaking bonds in the benzene ring and eventually the carbon backbone. By adding air or oxygen during the process, the polystyrene is oxidized, making it more hydrophilic. By introducing oxygen molecules to the polystyrene, a fine mosaic of hydrophilic and hydrophobic binding groups is generated with attract hydrophilic as well as hydrophobic regions on molecules. Substrates used in the culture method of the subject invention are generally not treated in this fashion, e.g., do not have a charged, hydrophilic surface.

Specific examples of cell attachment factors are those agents that include an RGD (Arginine-Glycine-Aspartic acid) cell attachment sequence of human fibronectin (Ruoslahti E. and Pierschbacher, M. D., *Science,* 238:491-497, 1987; Varani J. et al., *Cytotechnology,* 13:89-98, 1993; Lwebuga-Mukasa J. S., *American Journal of Respiratory Cell and Molecular Biology,* 10:347-354, 1994; Waldemar L. and Spear D., *Strategies in Molecular Biology,* 5:48-50, 1993; Stedronsky, E. R. et al., *Materials Research Society Symposium Proceedings,* 330:157-164, 1994). The RGD attachment sequence can be contained within structurally supportive peptide sequence, such as those of REACTI-BIND Treated Cell Culture Plates (PIERCE, Rockford, Ill.).

Some examples of cell attachment treatments that include chemical modification are photolithographic patterning of glass and subsequent silane/protein immobilization (Lom B. et al., *J. Neurosci. Methods,* 50:385-397, 1993), microcontact printing to localize phydrophobic alkanethiols/protein (Singhvi R. el al., *Science,* 264:696-698, 1994), photoimmobilization of polymers or adhesive peptides (Clemence J. F. et al., *Bioconjug. Chem.,* 6:411-417, 1995; Chen G. et al., *Bioconj. Chem.,* 8:730-734, 1997).

Some examples of cell attachment treatments that include physical modification of the substrate surface are microfluidic networks to deliver adhesive proteins or live cells directly (Chiu D. T. et al., *Proc. Acad. Sci. USA,* 97:2408-2413, 2000; Folch A. el al., *Biotechnol. Prog.,* 14:338-392, 1998; Delamarche E. et al., *Science,* 267:779-781, 1997).

Another cell attachment treatment involves coating a substrate, such as polyvinylchloride (PVC), with a thin layer of plasma deposited polymer, derived form acrylic acid, which provides a cell friendly layer that encourages cell attachment.

In one embodiment, the process-forming cells can be cultured in the presence of an attachment "blocking" agent, which deters or blocks the attachment of cells to the substrate. The blocking agent can be associated on or within the substrate or otherwise present within the cell culture. In this embodiment, the process-forming cells are, optionally, cultured on substrates that have cell attachment factors associated on or within the substrate or on substrates that are otherwise treated to promote cell attachment. Therefore, the blocking agents can inhibit the attachment of the cells, for example, by interfering with the cell attachment factor/cell attachment treatment. One example of a blocking agent that can be immobilized on a substrate surface is a non-adhesive PEO-based polymer, such as a PEO-terminated triblock polymer (Liu V. et al., *J. Biomed. Mater. Res.,* 60:126-134, 2002).

In another embodiment, the method of the subject invention involves culturing one or more process-forming cells under low calcium or calcium-free conditions. For example, the process-forming cells can be cultured in low calcium ($Ca^{2+}$) or calcium-free media. In another embodiment, the method of the subject invention involves culturing one or more process-forming cells on a solid substrate that lacks cell attachment factors or that has not been treated to promote cell attachment, as described above, wherein the cells are also cultured under low calcium or calcium-free conditions.

In each of the embodiments disclosed herein, the culture conditions are such that aggregation or clustering of individual cells is promoted and adhesion of the cells to the substrate is inhibited. Preferably, the process-forming cells attain a three-dimensional structure (forming a cluster of cells), grow process-free, with no attachment or minimal attachment to any supporting substrate, and are capable of reproducing cell-cell interactions in vitro which normally occur in vivo. Therefore, the cells can be manipulated in vitro and subsequently harvested without trauma to the cells.

As used herein, the terms "low calcium ($Ca^{2+}$), or "low calcium ($Ca^{2+}$) conditions", or grammatical variations thereof, with regard to the cell culture, are intended to mean a total calcium concentration of up to about 100 μM within the cell culture. Preferably, the calcium concentration of the cell culture is 50 μM or less. It is preferred that the culture medium utilized contains no calcium as a component, i.e., the media lacks $Ca^{2+}$ in its formulation; however, it is possible that contaminating levels of calcium (up to about 40 μM-50 μM) are present within water used to prepare the media. This situation also represents a "low calcium ($Ca^{2+}$) condition" according to the methods of the subject invention.

A variety of culture media can be utilized to culture process-forming cells according to the methods of the subject invention. For example, if low calcium conditions are desired, Minimum Essential Medium (MEM), Joklik modification for suspension culture, with L-Glutamine, without calcium chloride and sodium bicarbonate (SIGMA, St. Louis, Mo.; Product No. M0518), or other low calcium media can be used (Eagle, H. et al., *J. Biol. Chem.*, 214:845-847, 1956; Eagle, H., Media for Animal Cell Culture, Tissue Culture Association Manual, 3:517-520, 1976; Eagle, H., *Science*, 130:432-437, 1959; Eagle, H., *Science*, 122:501, 1955).

The subject invention also concerns cell therapy using process-forming cells that have been cultured according to the methods of the subject invention. A method for transplanting process-forming cells is carried out by culturing the cells according to the methods of the subject invention and subsequently administering the cells to a host, such as a human or animal. Transplantation of cultured cells can be carried out in order to treat a host that is susceptible to, or suffering from, a pathological condition, such as disease or trauma. However, transplantation of cultured cells can also be carried out as an elective procedure, such as elective cosmetic surgery.

For cell therapy, the cells cultured according to the methods of the subject invention can be harvested after about one week under the culture conditions of the subject invention, or when the cell clusters are within the range of about 150 μm and about 200 μm in diameter. Preferably, the cells are harvested before the cell clusters become so large in size that the cells inside of the cluster begin to degenerate. It is possible that degeneration of the innermost cells is caused by lack of nutrients penetrating beyond the outermost cell layers. Optionally, the harvested cells can be associated with a pharmaceutically acceptable carrier. For example, harvested cells can be placed in suspension with a pharmaceutically acceptable carrier. Optionally, cells cultured according to the methods of the subject invention can be differentiated through differentiation protocols before, during, or after harvest.

Examples of process-forming cells that can be cultured using the methods of the subject invention include, but are not limited to, neurons, glial cells, muscle cells, and endothelial cells. The process-forming cells to be cultured can be at various stages of differentiation. Optionally, process-forming cells can be co-cultured with other types of process-forming cells, or with non-process forming cells, such as Sertoli cells. These co-cultured cells can also be in various stages of differentiation and can include cells of various potencies, such as stem cells or specialized cells.

The Examples pertain to neuronal cells. The subject invention is particularly advantageous for the arrest of neurite extension to prevent cell death by axotomy, which usually occurs when the cells are detached from the conventional culture dishes to form a suspension for transplantation. Neurite extension is a general consequence of differentiation, which is desirable in cell transplant therapy in order to implant a fully functional cell and to minimize the risk that the cell will resort back to the cell cycle in vivo (which can be uncontrollable and can lead to tumor growth, for example). Advantageously, using the methods of the subject invention, neurite extension is arrested, and differentiation protocols can be applied to further differentiate the cells without neurite growth, thereby yielding a functional cell that will have enhanced survival post-detachment.

The subject invention also pertains to cell cultures comprising process-forming cells in the absence of cell attachment factors. Preferably, the process-forming cells are supported by a solid substrate lacking cell attachment factors, such as a microbiological plate, wherein the formation or extension of processes by the cells is inhibited. In another embodiment, the cell culture of the subject invention comprises a culture vessel or other solid support that contains or otherwise supports process-forming cells, wherein the cell culture is free of calcium or contains a low concentration of calcium, wherein the formation or extension of processes by the cells is inhibited by the low calcium concentration. Preferably, the cell culture comprises culture media that is either calcium-free or a low calcium media. In another embodiment, the cell culture comprises process-forming cells, a solid substrate lacking cell attachment factors, as described above, wherein the cell culture is free of calcium or contains a low concentration of calcium. For example, the cell culture can comprise process-forming cells, a solid substrate lacking cell attachment factors, and calcium-free or low calcium culture media.

Although the cultures of the subject invention are generally suspension cultures, all cultures of the subject invention are not necessarily suspension cultures. Depending upon the type of process-forming cells cultured, and their level of differentiation, some cells, such as cells of connective tissue (e.g., fibroblasts), may attach to substrates in the absence of attachment factors (such as untreated surfaces). Differentiated cells obtained from epithelia are much more dependant on matrix or charged surfaces.

Cells cultured according to the methods of the subject invention can be derived from humans, non-human mammals, or other animals, such as non-human primates, rodents, pigs, reptiles, amphibians, and fish, for example. Specific examples of source species include, but are not limited to, apes, chimpanzees, orangutans, humans, monkeys; domesticated animals (pets) such as dogs, cats, pigs, and rabbits; domesticated farm animals, such as cows, swine, sheep, and goats; and exotic animals.

Cells cultured according to the methods of the subject invention can be administered to a host in isolation or within a pharmaceutical composition comprising the cells and a pharmaceutically acceptable carrier. As used herein, a pharmaceutically acceptable carrier includes solvents, dispersion media, coatings, antibacterial and antifungal agents, isotonic agents, and the like. Pharmaceutical compositions can be formulated according to known methods for preparing pharmaceutically useful compositions. Formulations are described in a number of sources that are well known and readily available to those of ordinary skill in the art. For example, *Remington's Pharmaceutical Science* (Martin E. W., Easton Pa., Mack Publishing Company, 19th ed.) describes formulations that can be used in connection with the subject invention. Formulations suitable for parenteral administration, for example, include aqueous sterile injection solutions, which may contain antioxidants, buffers, bacteriostats, and solutes that render the formulation isotonic with the blood of the intended recipient; and aqueous and non-aqueous sterile suspensions that may include suspending agents and thickening agents. It should be understood that in addition to the ingredients particularly mentioned above, the formulations of the subject invention can include other agents conventional in the art having regard to the type of formulation and route of administration in question.

The cells cultured according to methods of the subject invention can be administered on or within a variety of carriers that can be formulated as a solid, liquid, semi-solid, etc. For example, genetically modified cells or non-genetically modified cells can be suspended within an injectable hydrogel composition (U.S. Pat. No. 6,129,761) or encapsulated within microparticles (e.g., microcapsules) that are administered to the patient and, optionally, released at the target anatomical site (Read T. A. et al., *Nature Biotechnology*, 2001, 19:29-34, 2001; Joki T. et al., *Nature Biotechnology*, 2001, 19:35-38; Bergers G. and Hanahan D., *Nature Biotechnology*, 2001, 19:20-21; Dove A. *Nature Biotechnology*, 2002, 20:339-343; Sarkis R. *Cell Transplantation*, 2001, 10:601-607).

Microcapsules can be composed of various polymers and, in addition to cells, their contents can include enzymes and other materials. Preferably, the microcapsules are prepared in such a way as to prevent their contents from leaking out and potentially causing an immunological reaction, while permitting nutrients and metabolites to exchange freely. The high surface-to-volume ratio of a spherical microcapsule facilitates maximal transport of nutrients, gases, or metabolites exchange across the membrane. In addition, encapsulation of living cells allows better control of the microenvironment for optimal cellular functions via selection of suitable substrates and incorporation of controlled release features, as described below. Such devices can be used to deliver various types of cells cultured according to the methods of the subject invention. Microcapsules can carry a payload of more than one type of cell. For example, neurons can be encapsulated with Sertoli cells and administered to a host.

Carriers are preferably biocompatible and optionally biodegradable. Suitable carriers include controlled release systems wherein the cells and/or the biological factors produced by the cells are released from the carrier at the target anatomic site or sites in a controlled release fashion. The mechanism of release can include degradation of the carrier due to pH conditions, temperature, or endogenous or exogenous enzymes, for example.

The cells cultured according to the methods of the invention can be administered in or on various scaffolds, such as synthetic or biological tissue scaffolds (Griffith G. and Naughton G., *Science*, 2002, 295:1009-1013; Langer R., *Stem Cell Research News*, Apr. 1, 2002, pp. 2-3). Porous scaffold constructs can be composed of a variety of natural and synthetic matrices, such as biominerals (e.g., calcium phosphate) and polymers (e.g., alginate) that are optionally cross-linked, and serve as a template for cell proliferation and ultimately tissue formation. Three-dimensional control of pore size and morphology, mechanical properties, degradation and resorption kinetics, and surface topography of the scaffold can be optimized for controlling cellular colonization rates and organization within an engineered scaffold/tissue construct. In this way, the morphology and properties of the scaffold can be engineered to provide control of the distribution of bioactive agents (e.g., proteins, peptides, etc.) and cells. In addition to use as vehicles for delivery of the cultured cells, scaffolds lacking cell attachment factors can be utilized to grow the cells in vitro. Optionally, cells can be cultured on the scaffolds themselves using the methods of the subject invention.

Scaffolds can contain interconnecting networks of pores and facilitate attachment, proliferation, and biosynthesis of cartilaginous matrix components, where desired. For example, synthetic or biological scaffolds carrying bone cells, such as chondrocytes, of the subject invention can be administered to a host in need thereof. Chitosan scaffolds, which are biocompatible and enzymatically degraded in vivo, can be seeded with chondrocytes cultured according to the methods of the subject invention and implanted. An alginate scaffold can be fabricated in the shape of a heart valve, seeded with cultured cells of the invention, and implanted within a host in need thereof. Because alginate does not naturally provide anchorage points for cells, in order to facilitate cell attachment, the peptide sequence R-G-D (Arginine-Glycine-Aspartic acid) can be utilized to act as a ligand for cell integrins and can be linked to alginate.

In the transplantation methods of the subject invention, cultured cells are preferably administered to a host in an amount effective to provide a therapeutic benefit. A "therapeutically effective amount" is that amount effective to treat a pathological condition. For purposes of the subject invention, the terms "treat" or "treatment" include preventing, inhibiting, reducing the occurrence of and/or ameliorating the physiological effects of the pathological condition to be treated. Preferably, the cells are administered to the host in an amount within the range of about $10^4$ to about $10^{10}$ cells. More preferably, the cells are administered to the host in an amount within the range of about $10^7$ to about $10^{10}$ cells. Doses of cells can be determined by one of ordinary skill in the art, with consideration given to such factors as cell survival rate following administration, the number of cells necessary to induce a physiologic response in the normal state, and the species of the host.

Cells can be genetically modified to produce various biomolecules, such as trophic factors or antibodies, as well as to exhibit any number of bioactive properties. Cells can be genetically modified before, during, or after culture according to the method of the subject invention. The various methods employed in the genetic modification of host cells are well known in the art and are described, for example, in Sambrook et al. (1989) *Molecular Cloning: A Laboratory Manual*, second edition, volumes 1-3, Cold Spring Harbor Laboratory, New York, and Gloves, D. M. (1985) *DNA Cloning, Vol. I. A Practical Approach*, IRL Press, Oxford. Thus, it is within the skill of those in the genetic engineering art to extract DNA from its source, perform restriction enzyme digestions, electrophorese DNA fragments, tail and anneal plasmid and insert DNA, ligate DNA, transform cells, e.g., prokaryotic and eukaryotic cells, prepare plasmid DNA, electrophorese proteins, and sequence DNA.

Cells cultured according to the methods of the subject invention can be differentiated using differentiation protocols, such as serum deprivation, or contacting the cells with one or more differentiation agents. The cells can be induced to differentiate further along particular developmental paths, depending upon the particular cell's plasticity and commitment to a particular differentiation pathway.

Depending upon cell type, differentiation of the cells can be induced by any method known in the art that activates the cascade of biological events that lead to cell growth. For example, following culture of the cells under conditions that inhibit process formation, cells can be induced to differentiate by plating the cells on a fixed substrate, such as a flask, plate, or coverslip, or a support of collagen, fibronectin, laminin, or extracellular matrix preparation such as MATRIGEL (Collaborative Research), removal of conditioned medium, serum, and addition of soluble modulators in the culture media. Cells can be incubated in dishes and on cover slips coated with MATRIGEL and subsequently seeded onto a treated surface (Cardenas, A. M. et al., *Neuroreport.*, 1999, 10:363-369). Differentiation can be induced by transfer to GM with 1% bovine serum and 10 μg/ml of both insulin and transferrin, wherein differentiating media is F12/D supplemented with 1% bovine serum and 1% stock supplement (Liberona, J. L. et al., *Muscle & Nerve*, 1998, 21:902-909). Horse serum can be utilized to increase fusion rate in myoblasts. Further differentiation procedures and agents can be found, for example, in Caviedes, R. et al., *Brain Research*, 1996, 365:259-268, where preconfluent cultures were incubated in complete growth medium plus 2% dimethylsulfoxide for 10 days, and in Arrigada, C. et al., *Amino Acids*, 2000, 18(4):363-373, where differentiation medium consisted of DMEM/Ham F12 nutrient mixture, supplemented with 2% adult bovine serum and 1% (v/v) of N3 supplement and 1% (v/v) Site+3 (SIGMA), and cells were allowed to differentiate for 1 week.

Cells can be stimulated to differentiate by contact with one or more differentiation agents (e.g., trophic factors, hormonal supplements), such as forskolin, retinoic acid, putrescin-transferrin, cholera toxin, insulin-like growth factor (IGF), transforming growth factor (e.g., TGF-α, TGF-β), tumor necrosis factor (TNF), fibroblast growth factor (FGF), epidermal growth factor (EGF), granulocyte macrophage-colony stimulating factor (GM-CSF), hepatocyte growth factor (HGF), hedgehog, vascular endothelial growth factor (VEGF), thyrotropin releasing hormone (TRH), platelet derived growth factor (PDGF), sodium butyrate, butyric acid, cyclic adenosine monophosphate (cAMP), cAMP derivatives (e.g., dibutyryl cAMP, 8-bromo-cAMP), phosphodiesterase inhibitors, adenylate cyclase activators, prostaglandins, ciliary neurotrophic factor (CNTF), brain-derived neurotrophic factor (BDNF), neurotrophin 3, neurotrophin 4, interleukins (e.g., IL-4), interferons (e.g., interferon-gamma), leukemia inhibitory factor (LIF), potassium, amphiregulin, dexamethasone (glucocorticoid hormone), isobutyl 3-methylxanthine, somatostatin, lithium, and growth hormone.

The subject invention also provides a ready source of cultured cells for research, including pharmacological studies for the screening of various agents, toxicologic studies for the cosmetic and pharmaceutical industries, and production of biomolecules for various purposes. The cultured cells can be used in methods for determining the effect of a synthetic or biological agent on cells. The term "biological agent" refers to any agent of biological origin, such as a virus, protein, peptide, amino acid, lipid, carbohydrate, nucleic acid, nucleotide, drug, pro-drug, or other substance that may have an effect on cells, whether such effect is harmful, beneficial, or otherwise.

The term "biomolecule" refers to any molecule that can be produced by genetically modified or non-genetically modified cells that are cultured according to the methods of the subject invention. Examples of biomolecules include viruses, proteins, peptides, amino acids, lipids, carbohydrates, nucleic acids, nucleotides, drugs, pro-drugs, or other substances that can be produced and found within the cell, on or within the cell membrane, or secreted by the cell. Therefore, the cultures and culture methods of the subject invention are also useful for the production of biomolecules in vivo or in vitro. The production of a particular biomolecule may be increased by the culture methods of the subject invention, relative to cells of the same type that are cultured conventionally in the presence of attachment factors. For example, as described in the Examples, the culture methods of the subject invention can be used to increase production of biomolecules such as melanin, which can be collected from the cells and purified. Optionally, cells used for production of biomolecules can be cultured in cell fermentors, or on or within beads, which maximizes culture surface and volume several, providing the opportunity to culture many more cells in a more reduced space.

As used herein, the term "process-forming cells" is intended to include those cells that are capable of forming cellular processes in vivo or in vitro, when cultured according to conventional culture techniques and/or when induced to do so using differentiation protocols, for example. Thus, in addition to neurons, process-forming cells that are not neurons are also contemplated. The process-forming cells can range in plasticity from totipotent or pluripotent stem cells, precursor or progenitor cells, to highly specialized or mature cells, such as those process-forming cells of the central nervous system (e.g., neurons and glia). For example, embryonic or adult stem cells or progenitor cells that are capable of forming cellular process in vivo or in vitro, or giving rise to such cells, can be cultured according to the methods of the subject invention. Other cells that can be cultured using the methods of the subject invention include, but are not limited to, neural cells, including nigral dopaminergic neurons of fetal, neonatal, and adult origins; glial cells from mesencephalon and striatum, of fetal, neonatal, and adult origins; GABAergic cells from various areas of the brain, including striatum or cortex, of fetal, neonatal, and adult origins; cholinergic neurons from the striatum, septum, and nucleus basalis, of fetal, neonatal, and adult origins; and serotogenic neurons derived from the lateral hypothalamus, dorsal raphe nucleus or hindbrain, of embryonic neonatal, or adult origins. Glial cells from numerous regions, including mesencephalon, striatum, cortex, subcortical white matter, spinal cord, or Schwann cells, of fetal, neonatal, and adult origins can be cultured using the methods of the subject invention. Almost all neuronal cells extend processes (neurites) in primary culture and are, hence, process-forming cells. Such neuronal cells can be obtained from brain cortex, hippocampus, spinal cord, dorsal root ganglion, autonomic ganglia, etc.). Other cells, such as chromaffin cells, and various cell lines are capable of process formation. Some specific examples of process-forming cell lines include hNT, C1300 and other neuroblastoma cell lines, CNh, CTb, RCSN, M4b, MTh, G4b, GTI, H4b, and HTk, which can be cultured according to the methods of the subject invention.

As used herein, the term "process" is intended to mean extensions that originate in the soma and grow in a centrifugal manner. Processes can extend to several times the diameter of the soma. Processes can also branch and, in culture, they can even make connections to other cells. For example, neurites (e.g., axons and dendrites) are processes that extend from the cell bodies of neurons.

As used herein, the term "host" is intended to include humans and non-human animals. Accordingly, cells cultured according to the method of the subject invention can be utilized for veterinary purposes. The transplanted cells can be allografts, autografts, or xenografts, for example.

As used herein, the terms "treat", "treatment", or grammatical variations thereof, within the context of hosts, refer to interventions that merely alleviate symptoms of a pathological condition, such as disease or trauma, or can even be curative in nature. These terms are also intended to include prophylaxis. The host can be suffering from a pathological condition, such as disease or trauma, wherein cell therapy is desired to alleviate the symptoms of the pathological condition. For example, neural cells cultured according to the methods of the subject invention can be administered to alleviate the symptoms of a neurological condition, such as a cognitive deficit. Examples of such neurological conditions include, but are not limited to, Alzheimer's disease, Parkinson's disease, Huntington's disease, ischemia, and brain trauma.

As used herein, the terms "administer", "apply", "transplant", "implant", "deliver", or grammatical variations thereof, are used interchangeably and intended to include all methods known in the art for delivery of cells to a host. For example, cells cultured according to the methods of the subject invention can be administered locally (e.g., to one or more target anatomical sites), systemically (e.g., through infusion), internally, etc. Cultured cells can be administered to a patient by any method of delivery, such as intravascularly, intracranially, intracerebrally, intramuscularly, intradermally, intravenously, intraocularly, orally, nasally, topically, or by open surgical procedure, depending upon the anatomical site or sites to which the cells are to be delivered. Cultured cells can be administered in an open manner, as in the heart during open-heart surgery, or in the brain during stereotactic surgery, or by intravascular interventional methods using catheters going to the blood supply of the specific organs, or by other interventional methods. The cells can be administered to various organs, such as the heart or brain. The methods of the subject invention contemplate intracerebral grafting of cultured cells to a region of the central nervous system (CNS), such as a region having sustained defect, disease, or trauma. Neural transplantation or "grafting" involves transplantation of cells into the central nervous system or into the ventricular cavities, or subdurally onto the surface of the host brain. The cells can be administered in isolation or as an active component in a pharmaceutical composition that also includes a pharmaceutically acceptable carrier, which can be solid, semi-solid, or liquid, for example. One or more types of process-forming cells can be cultured with one or more types of non-processing-forming cells, according to the method of the invention. The process-forming cells and/or the non-process-forming cells can then be removed from the culture for formulation as a pharmaceutical composition for subsequent implantation.

As used herein, the term "culture", or grammatical variations thereof, is intended to denote the maintenance or cultivation of cells in vitro, including the culture of single cells. Cultures can be cell, tissue, or organ cultures, depending upon the extent of organization.

As used herein, where the cells are described as being "supported by" a solid substrate, it is intended to include the situation where the substrate is supporting culture media containing the cells, wherein the cells are suspended in the culture media and not attached to the substrate.

As used herein, the term "isolated" means removal from its native environment, and can include removal from its immediate native environment. For example, a cell or cells can be isolated from an organism or from a primary culture.

As used herein, the term "differentiated" refers to those cells that maintain in culture all, or a substantial amount of, their specialized structure and function typical of the cell type in vivo. Partially differentiated cells maintain less than a substantial amount of their full complement of specialized structure and/or function. For example, the methods of the subject invention advantageously permit the culture of process-forming cells which, but for the inhibition of process formation or extension, maintain all or a substantial amount of their full complement of specialized structure and/or functions.

As used herein, the term "phenotype" refers to all the observable characteristics of a cell (or organism); its shape (morphology); interactions with other cells and the non-cellular environment (e.g., extracellular matrix); proteins or glycoproteins that appear on the cells surface (surface markers); and the cells' behavior (e.g., secretion, contraction, synaptic transmission).

The terms "comprising", "consisting of", and "consisting essentially of" are defined according to their standard meaning and may be substituted for one another throughout the instant application in order to attach the specific meaning associated with each term.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

Example 1

Culture of Process-Free Neurons

The RCSN-3 cell line (a rat substantia nigra cell line) was established from a primary culture of the striatum of Fisher 344 rats, and exposed to media conditioned with the UCHT1 cell line (Caviedes, R. and Stanbury, J. B., *Endocrinology*, 1976, 99:549-554). It has previously been determined that these cells (RCSN-3) retain their morphology according to the neuronal phenotype (Cardenas A. M. et al., *Neuroreport*, 1999, 10(2):363-369). However, exposure to UCHT1 or UCHT1 conditioned media is not required to carry out the culture methods of the subject invention.

Glial markers are absent in RCSN-3 cells. T-H and catecholamines are present. Neuronal markers expressed by RCSN-3 cells include neuronal specific enolase (NSE), MAP-2, neurofilament (NF), synaptophysin, tetanus toxin, paraformaldehyde glyoxilate, tyrosine hydroxylase, and melanin. The glial markers GFAP and S100 are not expressed by RCSN-3 cells.

RCSN-3 cells were cultured under conditions disfavoring attachment by seeding the cells on polystyrene microbiological plates that were not tissue culture treated. Cells were adapted to a low serum content culture media (2%) supplemented with hormones (insulin, progesterone), proteins (transferrins), and trace elements (sodium selenite, putrescine). These conditions produced spheroid-like cell aggregates that lack processes, which in turn permitted harvest of the cells without occurrence of axotomy. Cell aggregates of approximately 800 µm were formed in 3-4 weeks. Intrastriatal implantation of these aggregates has been performed on 6-OH dopamine lesioned rats. FIG. 1 shows the evolution in size of the cell aggregates (24 hours for the first, 3 days for the second, 1.5 weeks for the third, and 3 weeks for the last). The number of cells was estimated by measuring the diameter of the spheroids, and assuming that the aggregates form a sphere, the volume ($4/3\ \pi r^3$) was calculated. The diameter and volume of single cells was calculated the same way. Using a direct relation between volumes, the number of cells in each aggregate was calculated.

In a second stage of the experiment, the cells were grown in the presence of MATRIGEL in suspension. This reduced the time required for the formation of aggregates to 3 days. MATRIGEL is a reconstituted extracellular matrix preparation containing components that have a differentiating effect on various types of cells.

Example 2

Implantation of Cultured Neurons into Hemiparkinsonian Rat Model

Parkinson's disease is a chronic neurological condition caused by the degeneration of dopaminergic neurons, such as those of the substantia nigra. These neurons produce the neurotransmitter dopamine (DA). Low levels of DA are related to several symptoms (static movements, bradikinesia, depression, etc.).

6-OHDA was injected into the medial forebrain bundle in one hemisphere, which causes S.N. cells to degenerate. Apomorphine was used to challenge the imbalance produced in the levels of DA, thereby producing rotational effects in the rat. Transplantation of RCSN-3 cells that were cultured on microbiological plates, as described in Example 1, was carried out on the lesioned rats. Two different profiles were found. After transplantation, there was a decrease in the rotations per minute (rpms) observed in rats until a plateau phase was reached after 12 weeks. Upon dissection of transplanted rats, T-H$^+$ cells were found in the striatum, which could be transplanted material.

Figure 2:
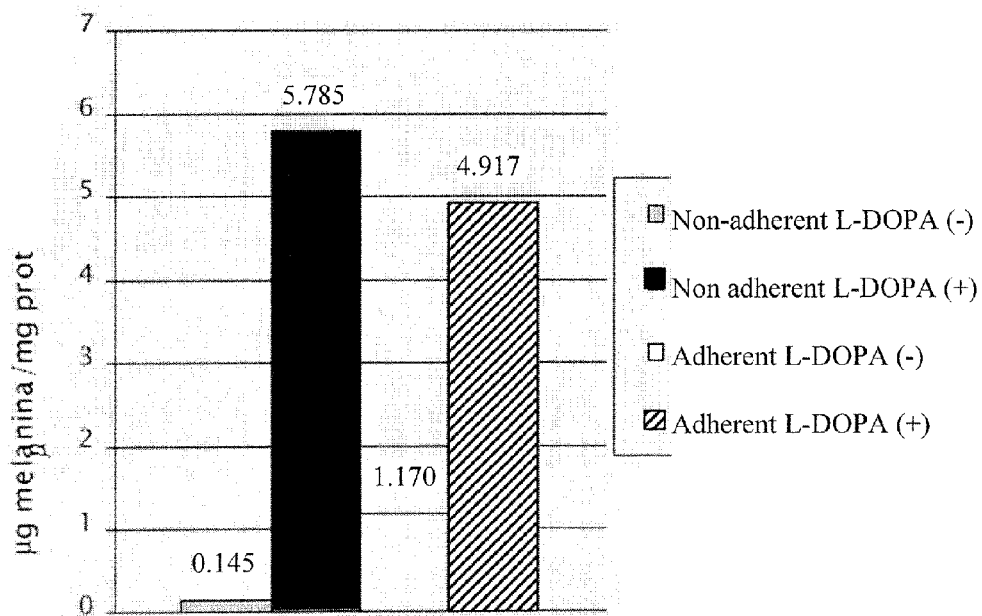
FIG. 2 shows the results of melanin measurements taken from RCSN-3 cells cultured using the method of the subject invention.
Figure 3A:
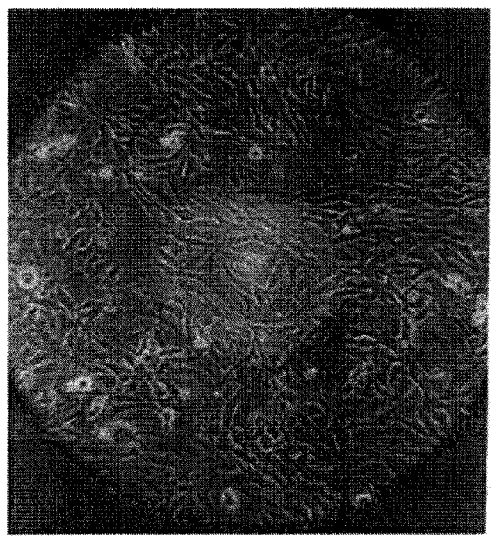
FIGS. 3A and 3B are micrographs showing monolayers of RCSN-3 cells cultured on treated cell culture dishes using standard growth media, with formation of neurites evident.
Figure 3B:
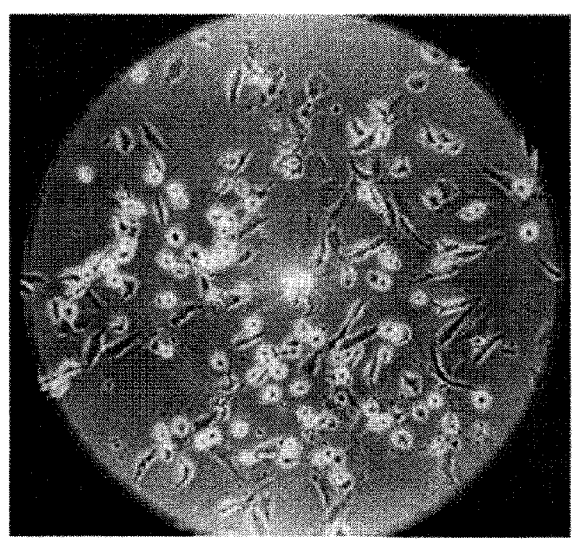
Figure 4A:
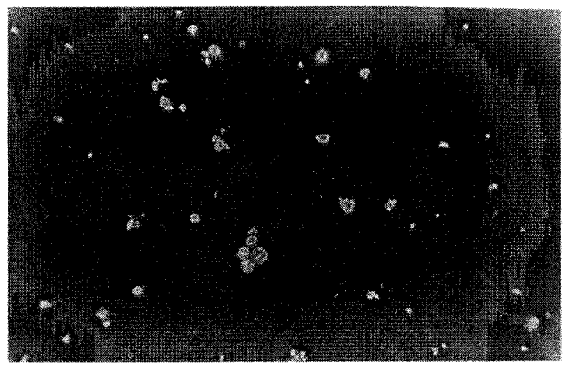
FIGS. 4A-4C are micrographs showing RCSN-3 cells cultured under conditions promoting clustering and inhibiting neurite formation, after 3 days, 10 days, and 21 days, respectively.
Figure 4C:
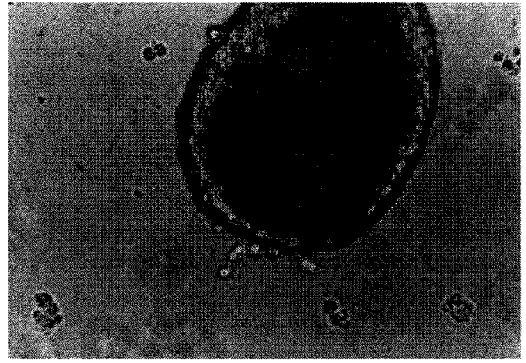
Figure 4B:
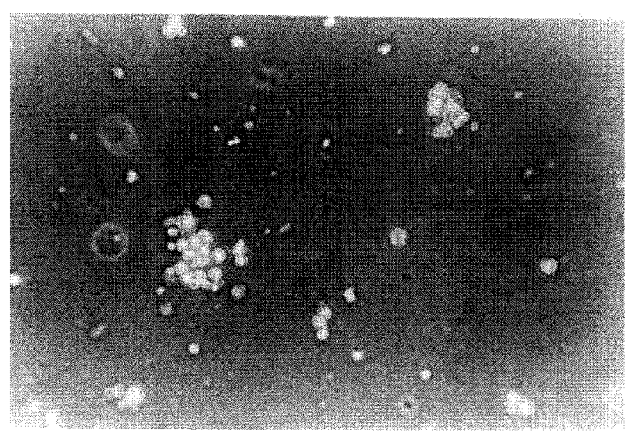

The most important enzyme present in RCSN-3 cells is tyrosine hydroxylase (T-H), which transforms tyrosine into 1-DOPA, a precursor of dopamine (DA). Subsequently, 1-DOPA is transformed to dopaquinone that assembles with other molecules of dopaquinone to form melanin. Melanin was measured as an indirect indicator of T-H presence in variable conditions. FIG. 2 shows results of melanin measurements. The cells cultured in plastic plates show a higher content of melanin in comparison with the cells grown under standard conditions (glass or plastic treated plates, 10% $CO_2$ atmosphere, DMEM:F12 1:1 supplemented with 10% bovine sera).

DA was also measured by high performance liquid chromatography (HPLC) using electrodetection methods. In these tests, it was found that DA is only produced when the precursor of 1-DOPA is added to the culture media. This indicates that TH expression is low. At present, culture media low in tyrosine is being investigated, since it has been documented that tyrosine can repress TH expression in melanoma cell lines.

We claim:

1. A method for cell therapy comprising removing one or more aggregates of process-forming cells from a cell culture; and administering the one or more aggregates of process-forming cells to a host, wherein cell culture comprises cell culture medium supported by a solid substrate, wherein the process-forming cells lack processes in the culture and cluster to form the one or more aggregates suspended in the cell culture medium, wherein the cell culture medium has a calcium concentration of 100 µM or less, and wherein the one or more aggregates are not attached to the solid substrate.

2. The method of claim 1, wherein the solid substrate comprises polystyrene and has an untreated surface for supporting the cell culture medium.

3. The method of claim 1, wherein the solid substrate has a surface supporting the cell culture medium, and wherein the surface lacks charged molecules.

4. The method of claim 1, wherein the solid substrate is a culture vessel selected from the group consisting of a Petri dish, flask, bottle, plate, tube, and vial.

5. The method of claim 1, wherein the solid substrate comprises untreated plastic.

6. The method of claim 1, wherein the solid substrate is a microbiological plate.

7. The method of claim 1, wherein the process-forming cells comprise neurons.

8. The method of claim 1, wherein the process-forming cells are selected from the group consisting of glial cells, muscle cells, connective tissue cells, and endothelial cells.

9. The method of claim 1, wherein the process-forming cells comprise two or more types of process-forming cells.

10. The method of claim 1, wherein the process-forming cells have been cultured with non-process-forming cells under conditions that are inhibitory to the formation or extension of cell processes.

11. The method of claim 1, wherein the process-forming cells are administered to the host with a pharmaceutically acceptable carrier.

12. The method of claim 1, wherein the host is human.

13. A method for cell therapy comprising:
culturing process-forming cells in cell culture medium on a solid substrate supporting the cell culture medium, wherein the process-forming cells lack processes in the culture and cluster to form the one or more aggregates suspended in the cell culture medium, wherein the cell culture medium has a calcium concentration of 100 µM or less, and wherein the one or more aggregates are not attached to the solid substrate; and
administering the one or more aggregates of process-forming cells to a host.

14. The method of claim 13, wherein the solid substrate comprises polystyrene and has an untreated surface for supporting the cell culture medium.

15. The method of claim 13, wherein the solid substrate has a surface supporting the cell culture medium, and wherein the surface lacks charged molecules.

16. The method of claim 13, wherein the solid substrate is a culture vessel selected from the group consisting of a Petri dish, flask, bottle, plate, tube, and vial.

17. The method of claim 13, wherein the solid substrate comprises untreated plastic.

18. The method of claim 13, wherein the solid substrate is a microbiological plate.

19. The method of claim 13, wherein the process-forming cells comprise neurons.

20. The method of claim 13, wherein the process-forming cells are selected from the group consisting of glial cells, muscle cells, connective tissue cells, and endothelial cells.

21. The method of claim 13, wherein the process-forming cells comprise two or more types of process-forming cells.

22. The method of claim 13, wherein said culturing comprises culturing the process-forming cells with non-process-forming cells under conditions that are inhibitory to the formation or extension of cell processes.

23. The method of claim 13, wherein the process-forming cells are administered to the host with a pharmaceutically acceptable carrier.

24. The method of claim 13, wherein the host is human.

* * * * *

UNITED STATES PATENT AND TRADEMARK OFFICE
CERTIFICATE OF CORRECTION

PATENT NO. : 8,252,279 B2
APPLICATION NO. : 11/951529
DATED : August 28, 2012
INVENTOR(S) : Pablo Caviedes et al.

It is certified that error appears in the above-identified patent and that said Letters Patent is hereby corrected as shown below:

Column 3,
Line 63, "generated with attract" should read --generated which attract--.

Column 4,
Line 31, "polymer, derived form acrylic" should read --polymer, derived from acrylic--.

Column 9,
Line 36, "isobutyl 3-methyulxanthine" should read --isobutyl 3-methylxanthine--.

Column 10,
Line 2, "and volume several," should read --and volume,--.

Signed and Sealed this
Eighteenth Day of December, 2012

David J. Kappos
*Director of the United States Patent and Trademark Office*